United States Patent [19]

Hatae et al.

[11] Patent Number: 4,847,074
[45] Date of Patent: Jul. 11, 1989

[54] WHITENING COSMETIC

[75] Inventors: Shinkichi Hatae, Ohnojo; Kazuo Nakashima, Noda, both of Japan

[73] Assignee: Sansho Seiyaku Co., Ltd., Ohnojo, Japan

[21] Appl. No.: 220,923

[22] Filed: Jul. 18, 1988

Related U.S. Application Data

[63] Continuation of Ser. No. 851,011, Apr. 11, 1986, abandoned.

[51] Int. Cl.$^4$ ................................................ A61K 7/00
[52] U.S. Cl. ........................................ 424/62; 514/58; 514/460; 514/844
[58] Field of Search .................. 424/62; 514/460, 844, 514/58

[56] References Cited

U.S. PATENT DOCUMENTS

| 2,827,452 | 3/1958 | Schlenk et al. | 514/58 |
| 4,278,656 | 7/1981 | Nagai et al. | 424/62 |
| 4,369,174 | 1/1983 | Nagai et al. | 514/460 X |
| 4,696,813 | 9/1987 | Higa | 424/59 |

FOREIGN PATENT DOCUMENTS

| 53-3538 | 1/1978 | Japan. | |
| 1109705 | 5/1986 | Japan | 514/844 |
| 2052973 | 2/1981 | United Kingdom. | |

OTHER PUBLICATIONS

Szejtli, J., *Proceedings of the First International Symposium on Cyclodextrins*, pp. 469-477 (1981).
Saruno et al., *Chemical Abstracts*, 89, 4582b (1978).
Kanebo Cosmetics, Inc., *Chemical Abstracts*, 96, 74507z (1982).
Yokota, *Chemical Abstracts*, 101, 116561s (1984).

*Primary Examiner*—John W. Rollins
*Assistant Examiner*—Wendy B. Catchpole
*Attorney, Agent, or Firm*—Jordan and Hamburg

[57] ABSTRACT

A whitening cosmetic comprises kojic acid and cyclodextrins in addition to cosmetic base materials. The kojic acid may be included in cyclodextrins before being incorporated into the cosmetic. The cosmetic has an improved stability against coloring with the passage of time and an enhance whitening effect. The cosmetic can be a toilet lotion, a cosmetic cream, a milky lotion, a pack, etc., for application to human skin.

5 Claims, No Drawings

WHITENING COSMETIC

This application is a continuation of application Ser. No. 851,011 filed Apr. 11, 1986, now abandoned.

BACKGROUND OF THE INVENTION

1. Field of the Invention

The present invention relates to a whitening cosmetic incorporated with kojic acid. In particular, it relates to a kojic acid-containing whitening cosmetic having not only an improved stability against discoloration but also an enhanced whitening effect.

2. Description of the Prior Art

Kojic acid, i.e., 5-hydroxy-2-hydroxymethl-$\gamma$-pyrone, is a compound which can be obtained by the fermentation of fungi of, e.g., Aspergillus genus. It is known that the compound functions as a tyrosinase inhibitor. Whitening cosmetics utilizing the function of the compound are known and disclosed in Japanese Patent Publication No. 18,569/81 and Japanese Patent Application (Laid Open) No. 3,538/78.

Whitening cosmetics, in particular cosmetic creams, containing kojic acid as an active ingredient are prone to a discoloration to yellowish brown when exposed to heat or light, and the density of the cosmetics tends to increase with the passage of time, thus impairing their value as an article to be marketed.

SUMMARY OF THE INVENTION

It is therefore an object of the present invention to provide a whitening cosmetic having an improved stability against coloring with the passage of time.

It is another object of the present invention to provide a whitening cosmetic having an enhanced whitening effect.

It has now been found that coloring can be markedly reduced and the whitening effect of kojic acid can be intensified when cyclodextrins are incorporated into a cosmetic in combination with kojic acid, or when kojic acid included in cyclodextrins is incorporated into a cosmetic.

Accordingly, there is provided by the present invention a whitening cosmetic having not only an improved stability against coloring but also an enhanced whitening effect, which comprises cyclodextrins and kojic acid, or kojic acid included in cyclodextrins.

DETAILED DESCRIPTION OF THE PREFERRED EMBODIMENTS

Kojic acid is a known compound obtainable by the fermentation of fungi belonging to such generics as Aspergillus, Penicillium, Gluconobacter, and the like.

Cyclodextrins to be used in the present invention in combination with kojic acid include $\alpha$-cyclodextrin, $\beta$-cyclodextrin and $\gamma$-cyclodextrin. Of these compounds, $\beta$-cyclodextrin can be most preferable.

Cyclodextrins can be used in an amount of from 0.5 to 10 parts by weight, per 1 part by weight of kojic acid.

Kojic acid can be included in cyclodextrins in advance to its incorporation into cosmetic base materials.

Inclusion of kojic acid in cyclodextrins can be carried out in the following manner: Cyclodextrins are dispersed in water, and then kojic acid is gradually added thereinto with stirring until they are completely dissolved. The thus prepared cyclodextrins and kojic acid, or kojic acid included in cyclodextrins, may be freeze dried.

In the above preparation, there can be used 0.5 to 10 parts by weight of cyclodextrins, per 1 part by weight of kojic acid. Most preferably, 4 parts by weight of cyclodextrins are used per 1 part by weight of kojic acid.

In the present invention, the combination of kojic acid and cyclodextrins or included kojic acid is incorporated into ordinary cosmetic base materials to prepare toilet waters or toilet lotions, cosmetic creams, cosmetic emulsions or milky lotions, packs, etc., which are to be applied to the human skin. Kojic acid may be incorporated into cosmetic base materials in an amount of from 0.01 to 2% by weight not only in the case where it is used together with cyclodextrins but also in the case where it is included in cyclodextrins before its incorporation into base materials.

The cosmetics of the present invention may be formulated into a toilet water or a cosmetic lotion. In preparing toilet waters or cosmetic lotions according to the present invention, moisturizers, skin nutrients, etc. are dissolved in purified water, and preservatives, perfumes, etc. are dissolved in an alcohol. The two solutions are then mixed at room temperature to give desired products. Kojic acid and cyclodextrins, or kojic acid included in cyclodextrins, can be added to the aqueous phase before mixing in an amount as described above.

The cosmetics of the present invention may be formed into a cream, which may be prepared as follows: Hydrophilic ingredients are added to purified water, for example, moisturizers such as glycerol and sorbitol, to form an aqueous phase. An oil phase is prepared by adding olephilic ingredients, such as preservatives and surfactants, into an oil, for example, solid oils such as bees wax, paraffins, microcrystalline wax, ceresine, higher fatty acids and hardened oils; semisolid oils such as vaseline, lanolin and glycerides; or liquid oils, such as squalane, liquid paraffin and various ester oils. The thus prepared aqueous and oil phases are heated to the same temperature, and the latter is gradually added to the former with gradual stirring and then emulsified to form a cream. Kojic acid and cyclodextrins, or kojic acid included in cyclodextrins, can be added to the aqueous phase in an amount as defined above.

The cosmetics of the present invention may also be utilized in the form of an emulsion or a milky lotion. In this case, the cosmetics of the invention may be prepared in accordance with the following method: A moisturizer such as glycerol is added to purified water, along with a pH adjuster, such as an acid or an alkali, and the like, and the resulting mixture is heated with stirring. Thereafter, ethanol is additionally added to the mixture to obtain an aqueous phase. Oily ingredients, such as preservatives and surfactants, are then added into an oil, for example, solid oils such as bees wax and paraffins; semisolid oils such as vaseline and lanolin; or liquid oils such as squalane, liquid paraffins and ester oils; and the resulting mixture is heated to give an oil phase. The oil phase is then added in the aqueous phase and subjected to a preliminary emulsification. Into the thus formed mixture is added protective colloidal agents, such as carboxyvinyl polymers and carboxymethyl cellulose, and the resulting mixture is uniformly emulsified by use of a homogenizing mixer to form a desired emulsion. Kojic acid and cyclodextrins, or kojic acid included in cyclodextrins, may be added to the liquid phase before emulsification in an amount as described above.

The cosmetics of the invention may also be prepared in a pack form, which may be prepared in any manner generally utilized for the production of packs. For example, into purified water are added moisturizers, such as glycerol, etc., film-forming agents, such as polyvinyl alcohols and bee gum, and other additives. The resulting mixture is then subjected to swelling. If desired, powders of such materials as kaolin, talc and zinc oxide may be additionally added to the mixture. Perfumes, preservatives, and the like are dissolved in ethanol. The ethanol solution is then mixed with the swelled product, and the resulting mixture is thoroughly kneaded to form a paste or cream. Kojic acid and cyclodextrins, or kojic acid included in cyclodextrins, can be added in any step of the above preparation, in an amount as stated hereinabove.

Preparation examples of included kojic acid, or kojic acid included in cyclodextrins, which is the active component in the cosmetics of the present invention, will be shown hereinbelow.

PREPARATION EXAMPLE

Into 0.5 to 4 parts by weight of $\beta$-cyclodextrin is added 1.5 to 12 parts by weight of purified water and stirred slowly. Thereafter, 1 part by weight of kojic acid is additionally added, and the resulting mixture is thoroughly stirred until a uniform dispersion is formed to give included kojic acid. The thus formed included kojic acid may be freeze dried.

|  | Percents by weight |
|---|---|
| Example 1: A cream | |
| 20% included kojic acid | 5.0 |
| Bees wax | 6.0 |
| Cetanol | 5.8 |
| Hydrogenated lanolin | 8.0 |
| Squalane | 30.0 |
| Glyceryl esters of fatty acids | 4.0 |
| Oleophilic glyceryl monostearate | 2.0 |
| Polyoxyethylene sorbitan monolaurate | 2.0 |
| Propylene glycol | 5.0 |
| Perfume | Appropriate amount |
| Preservative | Appropriate amount |
| Antioxidant | Appropriate amount |
| Purified water | 37.20 |
| Example 2: A cream | |
| Kojic acid | 1.0 |
| $\beta$-cyclodextrin | 4.0 |
| Bees wax | 6.0 |
| Cetanol | 5.8 |
| Hydrogenated lanolin | 8.0 |
| Squalane | 30.0 |
| Glyceryl esters of fatty acids | 4.0 |
| Oleophilic glyceryl monostearate | 2.0 |
| Polyoxyethylene sorbitan monolaurate | 2.0 |
| Perfume | Appropriate amount |
| Preservative | Appropriate amount |
| Antioxidant | Appropriate amount |
| Purified water | 37.20 |
| Example 3: A milky lotion | |
| 30% included kojic acid | 2.5 |
| Squalane | 5.0 |
| Vaseline | 2.0 |
| Bees wax | 0.5 |
| Sorbitan sesquioleate | 0.8 |
| Polyoxyethylene oleyl ether | 1.2 |
| Propylene glycol | 5.0 |
| Ethanol | 5.0 |
| Carboxyvinyl polymer (1% aqueous solution) | 20.0 |
| Potassium hydroxide | 0.1 |
| Perfume | Appropriate amount |
| Preservative and antioxidant | Appropriate amount |
| Purified water | 57.90 |
| Example 4: A milky lotion | |
| Kojic acid | 0.75 |
| $\beta$-cyclodextrin | 1.75 |
| Squalane | 5.0 |
| Vaseline | 2.0 |
| Bees wax | 0.5 |
| Sorbitan sesquioleate | 0.8 |
| Polyoxyethylene oleyl ether | 1.2 |
| Propylene glycol | 5.0 |
| Ethanol | 5.0 |
| Carboxyvinyl polymer (1% aqueous solution) | 20.0 |
| Potassium hydroxide | 0.1 |
| Perfume | Appropriate amount |
| Preservative and antioxidant | Appropriate amount |
| Purified water | 57.90 |
| Example 5: A pack | |
| 50% included kojic acid | 1.0 |
| Bee gum | 5.0 |
| Squalane | 2.0 |
| Propylene glycol | 5.0 |
| Zinc oxide | 10.0 |
| Kaolin | 10.0 |
| Ethanol | 5.0 |
| Perfume | Appropriate amount |
| Preservative | Appropriate amount |
| Purified water | 62.0 |
| Example 6: A pack | |
| Kojic acid | 0.5 |
| $\beta$-cyclodextrin | 0.5 |
| Bee gum | 5.0 |
| Squalane | 2.0 |
| Propylene glycol | 5.0 |
| Zinc oxide | 10.0 |
| Kaolin | 10.0 |
| Ethanol | 5.0 |
| Perfume | Appropriate amount |
| Preservative | Appropriate amount |
| Purified water | 62.0 |
| Example 7: A toilet lotion | |
| 40% included kojic acid | 2.0 |
| Citric acid | 0.4 |
| Calcium carbonate | 0.2 |
| Ethanol | 5.0 |
| Propylene glycol | 9.0 |
| Purified water | 82.4 |
| Perfume and preservative | Appropriate amount |
| Example 8: A toilet lotion | |
| Kojic acid | 0.5 |
| $\beta$-cyclodextrin | 1.5 |
| Citric acid | 0.4 |
| Calcium carbonate | 0.2 |
| Ethanol | 5.0 |
| Propylene glycol | 9.0 |
| Purified water | 82.4 |
| Perfume and preservative | Appropriate amount |

EXAMPLE 9

Test for coloring-preventing effects attainable by the active components of the invention
(1) Samples A: A cream prepared in Example 1, incorporated with 5% by weight of 20% included kojic acid (i.e., 1% by weight as kojic acid)

B: A cream prepared in Example 2, incorporated with 1% by weight of kojic acid and 4% by weight of β-cyclodextrin C: A cream incorporated with 1% by weight of kojic acid but not incorporated with cyclodextrins (2) Method of test The samples, A, B and C were allowed to stand for 2 months at a temperature of 45° C., and their lightness (L), redness (a), yellowness (b) and ΔE (color difference) were measured and compared with a control sample stored at a temperature of 5° C. for the same period of time, using Color Difference Meter Z-1001 DP produced by Nippon Denshoku Co., Ltd.

(3) Results of the test

Results obtained are shown in Table 1.

TABLE 1

| Samples | Lightness (L) | | Redness (a) | | Yellowness (b) | | Color Difference (ΔE) |
|---|---|---|---|---|---|---|---|
| | Measured Value | ΔL | Measured Value | Δa | Measured Value | Δb | |
| Control | 89.60 | — | −2.18 | — | 8.10 | — | 0 |
| A | 86.43 | −3.16 | −3.12 | −0.94 | 11.24 | 3.13 | 4.55 |
| B | 87.54 | −2.06 | −3.16 | −0.98 | 13.02 | 4.92 | 5.42 |
| C | 79.93 | −9.66 | −3.44 | −1.25 | 18.90 | 10.79 | 14.59 |

Note:
In the above table, ΔL, Δa, and Δb each shows [(sample value) − (control value)].

It is apparent from the results shown in Table 1 that Samples A and B, or cosmetics according to the present invention, have markedly reduced coloration compared with Sample C, in which kojic acid alone was incorporated.

EXAMPLE 10

Test of decoloring effect in cultured dye-producing cells (1) Samples
A: Kojic acid
B: 20% included kojic acid prepared in Preparation Example
C: Kojic acid and β-cyclodextrin
D: β-cyclodextrin (2) Method of test Mouse melanoma B16 cells were cultured in Eagle's MEM medium containing 10% fetal bovine serum and:
(1) 2.5 mM of kojic aicd [Test area A];
(2) 2.5 mM (reduced to kojic acid) of 20% included kojic acid (or kojic acid included in cyclodextrins at a percentage of 20%) prepared in the Preparation Example [Test area B];
(3) Kojic acid and β-cyclodextrin each in the same amount as used in Test area B [Test area C];
(4) β-cyclodextrin in the same amount as that of β-cyclodextrin contained in the inclusion compound used in Test area B [Test area D]; or
(5) Nothing [Test area E].

The samples were cultured at 37° C. for 6 days in an atmosphere consisting of 5% $CO_2$ and 95% air, then treated with tripsin, and subjected to centrifugation for 5 minutes at 2000 rpm to prepare cell pellets. The darkness of the thus prepared pellets were compared by naked eye.

(3) Results of test

Test area A showed a moderate fading, compared with Test area E (control).

Test areas B and C showed fading apparently stronger than that in Test area A, and the pellets obtained from these areas were white to light yellow in color.

Test area D showed no fading.

It is apparent from the above results that the active components of the present invention, namely included kojic acid and the combination of kojic acid and cyclodextrins, have effects of inhibiting the formation of melanine dyes, compared with the case where kojic acid alone is used.

What is claimed is:

1. A whitening cosmetic comprising cosmetic base materials, 0.01 to 2% by weight of kojic acid, based on the total weight of the cosmetic, and 0.5 to 10 parts by weight of cyclodextrin per 1 part by weight of said kojic acid.

2. A cosmetic as in claim 1, wherein the cyclodextrin is β-cyclodextrin.

3. A cosmetic as in claim 1, wherein the kojic acid is included in the cyclodextrin.

4. A cosmetic as in claim 1, wherein 4 parts by weight of cyclodextrin are present per 1 part by weight of kojic acid.

5. A cosmetic as in claim 1, wherein said cosmetic is selected from the group consisting of a cosmetic cream, a cosmetic emulsion, a milky lotion, a pack, a toilet water, and a toilet lotion.

* * * * *